(12) United States Patent
Sick et al.

(10) Patent No.: US 9,980,764 B2
(45) Date of Patent: May 29, 2018

(54) HANDLE FOR A SURGICAL INSTRUMENT, IN PARTICULAR A CRYOSURGICAL INSTRUMENT

(75) Inventors: Christian Sick, Nehren (DE); Markus Amann, Tuebingen (DE); Hansjoerg Besch, Gomaringen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 848 days.

(21) Appl. No.: 13/197,530

(22) Filed: Aug. 3, 2011

(65) Prior Publication Data
US 2013/0035678 A1 Feb. 7, 2013

(30) Foreign Application Priority Data

Aug. 4, 2010 (DE) .................. 10 2010 036 829

(51) Int. Cl.
*A61B 18/02* (2006.01)
*A61B 18/00* (2006.01)
*A61B 50/30* (2016.01)

(52) U.S. Cl.
CPC .......... *A61B 18/02* (2013.01); *A61B 18/0206* (2013.01); *A61B 2018/0091* (2013.01); *A61B 2018/0231* (2013.01); *A61B 2050/3011* (2016.02)

(58) Field of Classification Search
CPC ................ A61B 18/02; A61B 18/0206; A61B 2018/0005; A61B 2018/00011; A61B 2018/00017; A61B 2018/00023; A61B 2018/00035; A61B 2018/00047; A61B 2018/0231; A61B 2018/0243; A61B 2018/025; A61B 2018/0256; A61B 2018/0262

USPC ...................................................... 606/20–26
See application file for complete search history.

(56) References Cited

U.S. PATENT DOCUMENTS

| 3,958,818 | A | * | 5/1976 | Mason ..................... F16L 33/24 174/653 |
| 3,995,596 | A | * | 12/1976 | Andersson ............... A01K 7/06 119/71 |
| 4,712,813 | A | * | 12/1987 | Passerell et al. ............. 285/250 |
| 5,400,602 | A | * | 3/1995 | Chang .................... A61B 18/02 128/DIG. 27 |
| 5,928,154 | A | * | 7/1999 | Silber ..................... B25G 1/10 600/459 |
| 6,270,494 | B1 | * | 8/2001 | Kovalcheck ....... A61B 1/00142 600/121 |

(Continued)

FOREIGN PATENT DOCUMENTS

| CN | 2174961 Y | 8/1994 |
| DE | 600 26 041 T2 | 10/2006 |

(Continued)

*Primary Examiner* — Jaymi Della
*Assistant Examiner* — Eunhwa Kim
(74) *Attorney, Agent, or Firm* — Blank Rome LLP

(57) ABSTRACT

A handle for a surgical instrument, in particular a cryosurgical instrument, comprising a grip element and at least one sheathing tube that is inserted into the grip element and connected with said grip element in a fluid-tight manner in a connecting region. At least one support element is coaxially configured and arranged in the cavity of the sheathing tube such that the sheathing tube is clamped in place between the grip element and the support element in the connecting region.

14 Claims, 2 Drawing Sheets

(56) References Cited

U.S. PATENT DOCUMENTS

| | | |
|---|---|---|
| 6,440,126 B1 * | 8/2002 | Abboud ................. A61B 18/02 606/21 |
| 6,613,085 B1 * | 9/2003 | Anderson et al. ........... 623/2.11 |
| 6,746,055 B1 * | 6/2004 | Wood et al. .................. 285/249 |
| 7,160,291 B2 | 1/2007 | Damasco et al. |
| 7,207,985 B2 | 4/2007 | Duong et al. |
| 2003/0006610 A1 | 1/2003 | Werth |
| 2004/0148004 A1 * | 7/2004 | Wallsten ...................... 623/1.11 |
| 2004/0202561 A1 * | 10/2004 | Hershberger et al. ..... 417/477.7 |
| 2009/0163902 A1 | 6/2009 | DeLonzor et al. |
| 2009/0188575 A1 * | 7/2009 | Williams et al. ............. 137/798 |

FOREIGN PATENT DOCUMENTS

| | | |
|---|---|---|
| WO | WO 99/65410 | 12/1999 |
| WO | WO 2005/000106 A2 | 1/2005 |

\* cited by examiner

HANDLE FOR A SURGICAL INSTRUMENT, IN PARTICULAR A CRYOSURGICAL INSTRUMENT

FIELD OF THE INVENTION

Embodiments of the invention relate to a handle for a surgical instrument, in particular a cryosurgical instrument, comprising a grip element and at least one sheathing tube that is inserted into the grip element in a connecting region and is connected with said grip element in a fluid-tight manner.

BACKGROUND

In known handles, feed and discharge tubes are led via a sheathing tube to the grip element and fastened there to enable, for example, the fluid supply for a probe to which the handle can be attached. Such handles for surgical instruments have been known in the art.

When using surgical instruments, particular attention must be focused on sterility to ensure a safe intervention in the human body and to not unnecessarily jeopardize or prolong the healing of wounds following surgery. Considering this, there is a great demand for surgical devices and, in particular, handles for surgical instruments that, following use, can be machine-cleaned and processed, in particular, in suitable automatic washers.

As is known in the prior art, many such probes, handles and similar surgical devices are inherently unsuitable for automatic washers. As such, consequently, no seal was provided between the handle and the tubing. Mostly disposable parts were used. This represented a great environmental burden due to generated waste and use of large quantities of material; it also entailed high costs.

Until now, some flexible surgical probes resorted to the use of screw fittings to mechanically clamp the sheathing tube to the grip element. Such screw fittings have been used to create an additional seal between the sheathing tube and the grip element. In doing so, an additional integral compression spring, acting as a compression element, was intended to counteract any seating behavior resulting from thermal processing. However, in the long term, this did not guarantee a reliable seal because leaks still occurred due to thermal stress.

It is also known in the art to use silicone to create a seal between the sheathing tube and the grip element, in particular by gluing them together.

A further method is characterized in that the sheathing tube is molded on the grip element. However, in this case, a gap was formed between the sheathing tube and the tube, in particular due to an ovalizing of the tube when it was kinked, thus resulting in an infiltration of the tube by fluid or particles during the washing operation.

Publication DE 600 26 041 T2 discloses a protective sheathing tube that is suitable for use with a cryosurgical probe in a closed-cycle Joule-Thomson system. "Closed-cycle" means that the pressurized gas begins to circulate following expansion and is not discharged into the atmosphere. As a rule, these systems are permanently sealed to prevent the introduction of contaminants. The protective sheathing tube that is known in literature is slipped as an elastic component onto the probe so as to create a seal relative to the environment. Due to the sterile barrier achieved by the individual components, the probe can be used in a surgical procedure. This sheathing tube ensures the thermal conduction of the cryogenic probe tip by means of an integrally cast metal cap. The remainder of the sheathing tube consists of a material that is not thermally conductive such as, for example, a plastic material, and thus represents thermal insulation. However, the protective sheathing must be adapted to the exact design of each type of cryogenic probe to ensure a reliable fit. This is very time-consuming and expensive. Likewise, slipping-on the protective sheathing is fraught with difficulties because it must not be damaged for it to be able to fulfill its purpose of acting as a sterile cover for the components.

SUMMARY

Therefore, it is an object of the disclosed embodiments to provide a handle for a surgical instrument of the aforementioned type, such as a cryosurgical instrument, that can be cleaned, in particular machine-cleaned, with the use of an automatic washer without damaging the handle. In doing so, protection against fluid and particles, as well as a comfortable and safe use of the handle by the surgeon, is ensured.

This object is achieved by a handle for a surgical instrument such as a cryosurgical instrument, the handle comprising a grip element and at least one sheathing tube that is inserted into the grip element in the connecting region and sealed in a fluid-tight manner with said grip element, wherein at least one support element is configured and arranged in the cavity of the sheathing tube such that the sheathing tube is clamped between the grip element and the support element in the connecting region.

As mentioned above, feed and discharge elements are led to the grip element through such a sheathing tube and fastened there to enable, for example, a fluid supply to a probe that can be attached to the handle. These feed and discharge elements are tubes, for example, such as those necessary to convey the medium required for the individual surgical procedure to the probe and back again to the source.

An essential aspect of the disclosed embodiments is that a handle for a surgical instrument is designed such that it comprises a sealed transition between the grip element and the sheathing tube. This seal is formed with the sheathing tube supported on the inside by the grip element and this "supported" end of said sheathing tube being or will be clamped in place on the grip element end in a fluid-tight manner. Even if there are thermal stresses such as those that occur, for example, in automatic washers, any seating gaps between the grip element and the sheathing tube are prevented. Accordingly, a gap formation between the sheathing tube and the grip element is avoided, and an infiltration of fluid or particles into the grip element is prevented. Due to this seal, the handle is suitable for automatic washers, and its sterility can be ensured.

It should be appreciated that the inventive handle can be used with any type of apparatus-assisted surgery such as, for example, cryosurgery, radio-frequency (RF) surgery, water jet surgery, ophthalmic surgery, etc.

By inserting or accommodating a support element in the cavity of the sheathing tube, the sealing transition from the grip element onto the sheathing tube is supported. Because of the support element, the sheathing tube is pushed or pressed against the grip element and thus is securely clamped in between. In doing so, this counteracts any kinking of the sheathing tube, and the sealing effect of the connection of sheathing tube and grip element is enhanced.

Preferably, the connecting region is provided at the proximal end of the grip element. The transition from the grip element to the sheathing tube is optimally stabilized by the support element in the connecting region and thus counteracts any kinking of the sheathing tube at the proximal end of the grip element.

Preferably, the grip element consists at least partially of an elastic end element in the connecting region, or the grip element has an elastically designed end element in the connecting region. Such an embodiment ensures that the grip element will always adapt to the sheathing tube to create a seal as a result of the elastic configuration in the connecting region and, in particular, at the transition to the sheathing tube and thus is or remains securely connected therewith.

The remainder of the grip element, i.e., in the distal region, is preferably fashioned of a polymer that is harder and stiffer than the elastic end element of the grip element, said polymer being polyamide (PA) or polypropylene (PP). Due to the resultant haptic properties of the grip element, safe handling of the surgical instrument is made possible for the user.

The elastic end element of the grip element is preferably fashioned of a thermoplastic elastomer that contracts when a temperature increase occurs. As a result, the adaptation to the sheathing tube can be optimized and the sealing effect enhanced because the thermoplastic material will additionally shrink later during thermal processing. Furthermore, silicone can be used as the elastic end element.

Preferably, the elastic end element of the grip element is molded on and around the sheathing tube, or fastened in a similar manner. Using this fastening technique, the sealing effect can be ensured in a lasting manner, because the elastic element will "cling" directly to the sheathing tube and the grip element in the connecting region. An infiltration of the grip element by fluid or particles can be prevented, and an optimally sealed transition can be formed.

In a preferred manner, the support element is configured as a bushing. This bushing is inserted into the sheathing tube, slightly expanding said sheathing tube and thus optimally supporting said sheathing tube. In particular, in the connecting region, the sheathing tube can no longer change its shape such that the sheathing tube can be kinked in this region. To this extent, the sealing effect is decisively improved.

A proximal end of the support element preferably projects from the connecting region of the grip element. This causes the sheathing tube to be supported beyond the connecting region and the elastic element of the grip element, causing the sealing transition of the handle to the sheathing tube of the tubing set to be stabilized. In particular, the forming of a gap due to an ovalizing of the sheathing tube (when there is a kink) is prevented. In a preferred manner, the support element projects by a length of about 1 mm to 10 mm, particularly 5 mm.

Preferably, the handle comprises at least one clamping element that clamps the sheathing tube, at its distal end, in place on the support element. The distal end of the sheathing tube that is slipped over the support element is fastened, with an additional clamping element, to the support element and secured, and, in so doing, is accommodated in the grip element. This ensures that the sheathing tube is held firmly in the grip element.

In a preferred manner, the clamping element is a clamping ring that can be slipped over the sheathing tube in the direction of a clamping surface on the support element such that the sheathing tube is clamped in place between the clamping surface and the clamping ring. The sheathing tube is pressed against the—in particular slightly beveled—clamping surface of the support element such that the clamping ring having a slightly beveled complementary surface extending in opposite direction adapts to the beveled clamping surface of the support element. Consequently, the fit and the firm and secure seat of the sheathing tube on the support element, respectively, are optimized. In doing so, the sheathing tube is secured against slipping or sliding off the support element.

Preferably, at least one sealing element such as an O-ring is interposed between the grip element and the sheathing tube and/or between the sheathing tube and the support element. This sealing element is arranged so as to circumscribe the sheathing tube in axial direction of the sheathing tube behind the clamping ring in a recess of the hard element of the grip element. Consequently, an additional sealing element is attained in the handle of the surgical instrument to prevent an infiltration of fluid or particles into the interior of the surgical instrument. Also, this additional sealing element improves the seat of the sheathing tube on the support element and inside the grip element so that said sealing element helps secure the sheathing tube in its position.

Additional embodiments of the invention are obvious from the dependent claims.

BRIEF DESCRIPTION OF THE DRAWINGS

Hereinafter, embodiments of the invention will be described in greater detail with reference to the drawings, in which.

DETAILED DESCRIPTION

In the following description, the same parts and parts acting in the same manner have the same reference symbols, although in some instances a prime is added.

Figure 1:
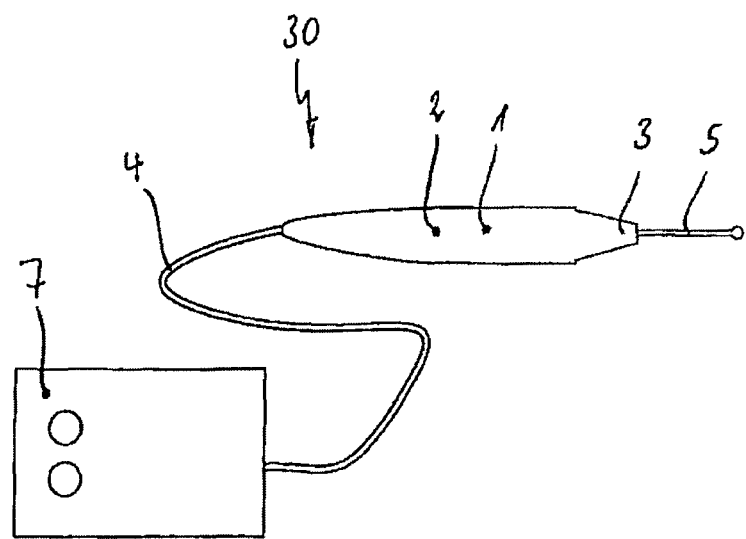
FIG. 1 is a schematic representation of a surgical instrument with a supply unit.

FIG. 1 is a schematic representation of a surgical instrument 30 and a supply unit 7. The surgical instrument 30 comprises a handle 1 with a grip element 2, and a probe head 3 with a probe tip 5. Said surgical instrument is connected to the supply unit 7 via a sheathing tube 4 that guides a feed line 9 and a return line 9 (see FIG. 2). In this embodiment, the supply unit 7 is the source for any supply or supply media, depending on the field in which the surgical instrument is being used. Such supply media are, for example, alternate current for radio-frequency (RF) surgery, coolants—preferably liquid nitrogen—for cryosurgery, or water for water jet surgery, etc.

Figure 2:
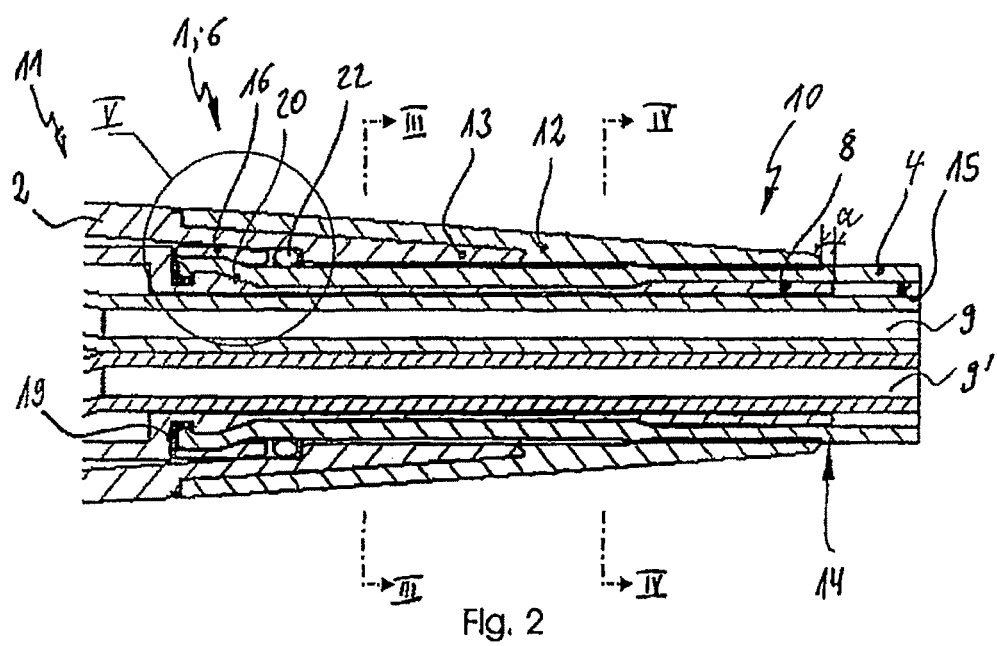
FIG. 2 illustrates a longitudinal section through a handle of the surgical instrument shown in FIG. 1.

FIG. 2 illustrates a longitudinal section through the handle 1 of the surgical instrument 30 in the connecting region 6, i.e., the region where the sheathing tube 4 is connected with the grip element 2. As previously mentioned, two tubes 9, such as a feed line and a return line, are inserted into the handle 1 and in the sheathing tube 4. Said feed and return lines convey the medium required for the surgical procedure to and away from the surgical instrument 30.

The connecting region 6 is located at the proximal end 10 of the grip element 2. Using a support element—in this case a bushing 8 that is arranged in the cavity 15 of the sheathing tube 4 and is slipped into the sheathing tube 4 while expanding said sheathing tube—the sheathing tube 4 is clamped in place relative to the grip element 2. In accordance with the disclosed embodiment, the bushing 8 is disposed to securely support the sheathing tube 4 in the connecting region 6 and, in particular, to act as protection against an ovalizing or kinking at the proximal end 10.

Preferably, a radially peripheral clamping surface 20 is provided on the bushing 8 where the sheathing tube 4 fits snugly. To optimize the attachment of the sheathing tube 4 to the bushing 8, it is possible to slip a clamping element such as a clamping ring 16 over the sheathing tube 4. In addition, the sheathing tube 4 in this embodiment is hooked in a recess 19 to ensure positional stability in the axial direction.

In the illustrated embodiment, a sealing element such as an O-ring 22 is interposed behind the clamping ring 16 to provide an additional seal for the handle 1.

A hard element 13 is formed on the distal end 11 of the grip element 2. An elastic end element 12 of the grip element 2 is provided in the connecting region 6 between the grip element 2 and the sheathing tube 4. In the illustrated embodiment, the elastic end element 12 is molded onto the sheathing tube 4 and the hard element 13. In doing so, the elastic end element 12 forms an elastic protective sleeve that, to a certain extent, follows the movements of the sheathing tube; said protective sleeve ensuring the sealing transition between the grip element 2 and the sheathing tube 4 and, in particular, preventing the infiltration of fluid or particles from the environment.

This sealing effect is enhanced by the bushing 8 because the bushing 8 additionally expands the sheathing tube 4, pressing said sheathing tube against the elastic end element 12. Consequently, the surgical instrument 30 is suitable for an automatic washer and can be optimally cleaned and sterilized in an automatic cleaning device to be subsequently reused for a surgical procedure.

The elastic end element 12 is made of a thermoplastic material that constricts with cyclic temperature fluctuations, i.e., specifically when being successively heated and then cooled. Due to the increased temperature during the cleaning operation and subsequent cooling, the elastic end element 12 constricts due to its thermoplastic properties, thus enhancing the sealing effect.

In the connecting region 6, the proximal end 14 of the bushing 8 projects by a length a beyond the proximal end 10 of the grip element 2. This length a is, for example, between 1 mm and 10 mm, particularly 2 mm. As a result, the support of the sheathing tube 4 is increased; any kinking and resulting ovalizing combined with the formation of a gap are thus prevented. Consequently, the elastic end element 12 of the grip element 2 cannot be infiltrated by fluid or particles.

Figure 3:
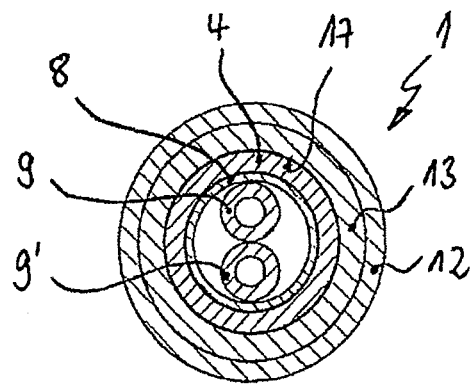
FIG. 3 illustrates a cross-section through the handle shown in FIG. 2.

FIG. 3 shows a cross-section through the handle of FIG. 1 along the intersecting line III-III of FIG. 2 in the connecting region 6 of said handle. Inside the surgical instrument 30, two tubes 9 can be seen, said tubes representing feed and return lines. These two tubes 9 lead through the bushing 8 into the handle 1 of the surgical instrument 30. The bushing 8 supports the sheathing tube 4 such that said sheathing tube is clamped against the interior wall 17 of the grip element 2 and its hard element 13 in a secure and fluid-tight manner.

As mentioned, this hard element 13 of the grip element 2 circumscribes the entire circumference of the sheathing tube 4. Sealing the grip element 2, the elastic end element 12 is arranged on the hard element 13, said elastic element forming the sealing transition between the hard element 13 of the grip element 2 and the sheathing tube 4 and is molded onto the hard element 13. In this way, it is possible, among other things, to ensure safe handling and protection against the infiltration of fluid or particles from the environment. Instead of being molded on, it is also possible to slip the elastic end element 12 as an elastic sheath over the hard element 13 and the sheathing tube 4, and to design it in particular in such a manner that said elastic element actively presses the sheathing tube 4 onto the support element 8.

Figure 4:
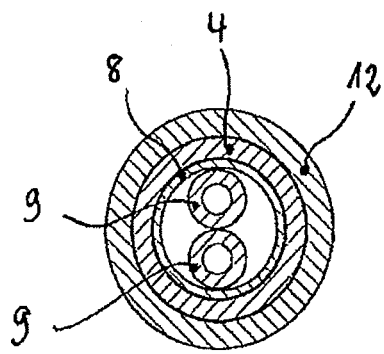
FIG. 4 illustrates a cross-section through the handle shown in FIG. 2.

FIG. 4 shows a cross-section through the handle of FIG. 1, along an intersection line IV-IV in accordance with FIG. 2 in the proximal end region 10 of said handle. The shown components essentially correspond to the illustration of FIG. 3; however, in this illustration, the elastic end element 12 can be seen as being also directly fastened to or mounted onto the sheathing tube 4.

Figure 5:
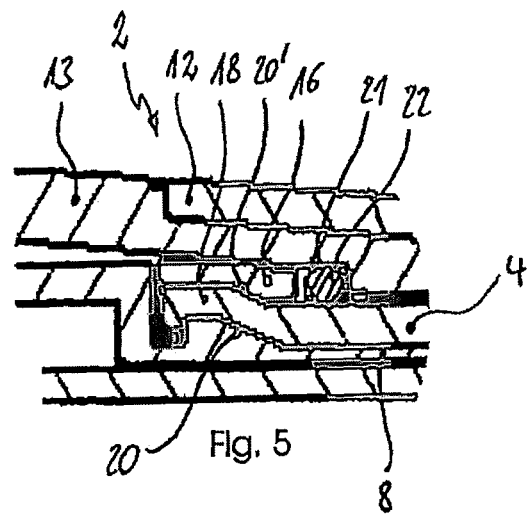
FIG. 5 illustrates details of the locking region identified in FIG. 2.

FIG. 5 is a view of details V of the locking region of the sheathing tube as identified in FIG. 2. To optimize the attachment of the distal end 18 of the sheathing tube 4 to the bushing 8, a clamping element such as a clamping ring 16 can be slipped over the sheathing tube 4 in the direction of the clamping surface 20. This clamping ring 16 also has a clamping surface 20' that has a bevel complementary to the bevel of the clamping surface 20 of the bushing 8.

To create an additional seal, a sealing element such as an O-ring 22 is interposed behind the clamping ring 16. A recess 21 for this O-ring 22 is located in the grip element 2 to enable a secure fit of the O-ring 22. This recess 21 is provided in the hard element 13 of the grip element.

Referring to this exemplary embodiment, it can also be clearly seen that the elastic end element 12 is directly attached to the hard element 13 of the grip element 2 and is directly attached—in the direction of the proximal end 10 (see FIG. 2)—to the sheathing tube 4, i.e., preferably by being molded on. This results in a doubly sealed transition to the sheathing tube 4. This transition and its sealing effect are further enhanced in case of a temperature increase (heating) and a subsequent temperature decrease (cooling) because the elastic end element 12 exhibiting special thermoplastic properties will additionally shrink when the temperature is increased and subsequently decreased, and will contract on the sheathing tube 4 and the hard element 13 of the grip element 2, pressing them even more snugly against each other. In doing so, a safe and optimal seal on the surgical instrument 30, as well as an optimal seal against moisture or particles from the environment during the cleaning or sterilization operation, or during a surgical procedure in any surgical field, can be ensured.

The invention claimed is:

1. A handle for a surgical instrument, said handle comprising:
    a grip element connected to a supply unit via a plurality of tubes and comprising a hard element;
    a sheathing tube surrounding the plurality of tubes, the sheathing tube being arranged to guide the plurality of tubes into the grip element, being hooked in a recess of the grip element to ensure positional stability in the axial direction and being connected in a fluid-tight manner with said grip element in a connecting region;
    a support element being configured and arranged coaxially within the sheathing tube and surrounding the plurality of tubes such that the sheathing tube is clamped between the grip element and the support element in the connecting region; and
    at least one clamping element that clamps the sheathing tube in place on the support element,
    wherein the grip element consists at least partially of an elastic end element in the connecting region, the elastic end element comprising an elastic protective sleeve that at least partially follows the movements of the sheathing tube and prevents infiltration of fluid or particles from the environment, wherein the elastic end element is provided in the connecting region and is molded onto the sheathing tube and the hard element, wherein the at least one clamping element is a clamping ring that can be coaxially slipped over the sheathing tube in the direction of a clamping surface on the support element such that the sheathing tube is clamped in place between the clamping surface and the clamping ring, wherein the clamping ring has a beveled clamping surface that is complementary to a beveled surface of the clamping surface on the support element, wherein the at least one clamping element clamps a distal end of the sheathing tube, and wherein a proximal end of the support element projects from the connecting region of the grip element such that the sheathing tube is supported beyond the connecting region and the elastic end element, thereby stabilizing a sealing transition of the grip element to the sheathing tube.

2. The handle of claim 1, wherein the connecting region is provided at a proximal end of the grip element.

3. The handle of claim 1, wherein the elastic end element is comprised of a plastic material that contracts when a temperature increase occurs.

4. The handle of claim 3, wherein the plastic material is a thermoplastic elastomer.

5. The handle of claim 1, wherein the elastic end element is molded around the sheathing tube.

6. The handle of claim 1, wherein the support element is configured as a bushing.

7. The handle of claim 1, wherein a proximal end of the support element projects beyond the connecting region by a length between 1 mm to 10 mm.

8. The handle of claim 7, wherein a proximal end of the support element projects beyond the connecting region by a length of about 5 mm.

9. The handle of claim 1, further comprising at least one sealing element interposed between the grip element and the sheathing tube.

10. The handle of claim 9, wherein each of the at least one sealing element is an O-ring.

11. The handle of claim 1, further comprising at least one sealing element interposed between the sheathing tube and the support element.

12. The handle of claim 11, wherein each of the at least one sealing element is an O-ring.

13. The handle of claim 1, wherein the elastic end element is not included in the at least one clamping element.

14. The handle of claim 1, wherein the at least one clamping element is positioned between the elastic end element and the sheathing tube.

* * * * *